(12) United States Patent
Heuer et al.

(10) Patent No.: US 7,794,749 B2
(45) Date of Patent: Sep. 14, 2010

(54) RAPIDLY DISSOLVING SOLID ORAL DOSAGE FORM FOR DELIVERY OF COMPOSITION FOR INCREASING NITRIC OXIDE ACTIVITY

(75) Inventors: Marvin A. Heuer, Mississauga (CA); Kenneth Clement, Mississauga (CA); Shan Chaudhuri, Mississauga (CA)

(73) Assignee: Northern Innovations and Formulations Corp.

( * ) Notice: Subject to any disclaimer, the term of this patent is extended or adjusted under 35 U.S.C. 154(b) by 79 days.

(21) Appl. No.: 11/505,779

(22) Filed: Aug. 16, 2006

(65) Prior Publication Data

US 2007/0196470 A1 Aug. 23, 2007

Related U.S. Application Data

(60) Provisional application No. 60/776,325, filed on Feb. 23, 2006.

(51) Int. Cl.
*A61K 9/22* (2006.01)
*A61K 47/00* (2006.01)
*A61K 31/44* (2006.01)

(52) U.S. Cl. .................. 424/468; 424/439; 514/335

(58) Field of Classification Search ............... None
See application file for complete search history.

(56) References Cited

U.S. PATENT DOCUMENTS

| | | | |
|---|---|---|---|
| 4,781,925 A | 11/1988 | Michelucci | |
| 5,145,684 A * | 9/1992 | Liversidge et al. | 424/489 |
| 5,955,107 A | 9/1999 | Augello | |
| 6,245,352 B1 | 6/2001 | Arbuthnot et al. | |
| 6,599,530 B2 | 7/2003 | Vahervuo | |
| 6,599,531 B2 | 7/2003 | Kushla | |
| 7,049,283 B2 | 5/2006 | Ault | |
| 7,081,255 B2 | 7/2006 | Baert | |
| 2005/0079216 A1* | 4/2005 | Petereit et al. | 424/464 |
| 2005/0282870 A1* | 12/2005 | Carter et al. | 514/355 |
| 2005/0287210 A1* | 12/2005 | Ron | 424/468 |

FOREIGN PATENT DOCUMENTS

DE  WO 03/072087  *  9/2003

OTHER PUBLICATIONS

Remington: The Science and Practice of Pharmacy (1995); p. 595.*
Reference website showing that xanthinol nicotinate and xantinol nicotinate have the same CAS Reg. No. (http://209.85.215.104/search?q=cache:caeE_RNsU08J:www.buyersguidechem.com/AcasAus.php%3Fcass%3D437-74-1%26herk%3D.AbcE.AbcA+%22xantinol+nicotinate%22+%22xanthinol+nicotinate%22+CAS&hl=en&ct=clnk&cd=7&gl=us).*
Adams et al., Oral L-arginine improves endothelium-dependent dilatation and reduces monocyte adhesion to endothelial cells in young men with coronary artery disease. Atherosclerosis. Mar. 21, 1997;129(2):261-9.
Appleton et al., Clinical potential of a semi-essential amino. Altern Med Rev. Dec. 2002;7(6):512-22.
Barbul et al., Arginine: biochemistry, physiology, and therapeutic implications. JPEN J Parenter Enteral Nutr. Mar.-Apr. 1986;10(2):227-38.
Bieron et al., Thrombolytic and antiplatelet action of xanthinol nicotinate (Sadamin): possible mechanisms. J Physiol Pharmacol. Jun. 1998;49(2):241-9.
Bradley et al., Nitric oxide synthase inhibition reduces leg glucose uptake but not blood flow during dynamic exercise in humans. Diabetes. Sep. 1999;48(9):1815-21.
Folland et al., The influence of nitric oxide on in vivo human skeletal muscle properties. Acta Physiol Scand. Jun. 2000;169(2):141-8.
Hallemeesch et al., Reduced arginine availability and nitric oxide production. Clin Nutr. Aug. 2002;21(4):273-9).
Hambrecht et al., Correction of endothelial dysfunction in chronic heart failure: additional effects of exercise training and oral L-arginine supplementation. J Am Coll Cardiol. Mar. 1, 2000;35(3):706-13.
Kaliman et al., Insulin-like growth factor-II, phosphatidylinositol 3-kinase, nuclear factor-kappaB and inducible nitric-oxide synthase define a common myogenic signaling pathway. J Biol Chem. Jun. 18, 1999;274(25):17437-44.
Kobzik et al., Nitric oxide in skeletal muscle. Nature. Dec. 8, 1994;372(6506):546-8.
Kubota et al., L-arginine increases exercise-induced vasodilation of the forearm in patients with heart failure. Jpn Circ J. Jun. 1997;61(6):471-80.
Loriaux et al., The effects of nicotinic acid and xanthinol nicotinate on human memory in different categories of age. A double blind study. Psychopharmacology (Berl). 1985;87(4):390-5).
Maxwell et al., L-arginine enhances aerobic exercise capacity in association with augmented nitric oxide production. J Appl Physiol. Mar. 2001;90(3):933-8.
Nathan C. Nitric oxide as a secretory product of mammalian cells. FASEB J. Sep. 1992;6(12):3051-64.
Preli et al., Vascular effects of dietary L-arginine supplementation. Atherosclerosis. May 2002;162(1):1-15.
Rector et al., Randomized, double-blind, placebo-controlled study of supplemental oral L-arginine in patients with heart failure. Circulation. Jun. 15, 1996;93(12):2135-41.
Shu et al., Studies of rapidly disintegrating tablets in the oral cavity using co-ground mixtures of mannitol with crospovidone. Chem Pharm Bull (Tokyo). Feb. 2002;50(2):193-8.
Stamler et al., Physiology of nitric oxide in skeletal muscle. Physiol Rev. Jan. 2001;81(1):209-237.

(Continued)

*Primary Examiner*—Robert A Wax
*Assistant Examiner*—Jeffrey T Palenik

(57) ABSTRACT

The present invention relates to a dietary supplement and method for a rapidly dissolving and disintegrating solid oral dosage form. Specifically, the present invention provides dietary supplements and methods for the delivery of dietary supplements comprising Arginine or derivatives thereof and Xanthinol Nicotinate or derivatives thereof. By way of oral administration to an individual of said solid oral dosage form, a method of rapidly increasing nitric oxide activity in an individual is also provided.

39 Claims, No Drawings

OTHER PUBLICATIONS

Tidball et al., Mechanical loading regulates NOS expression and activity in developing and adult skeletal muscle. Am J Physiol. Jul. 1998;275(1 Pt 1):C260-6.

Wade et al., Handbook of Pharmaceutical Excipients, Second Edition, The Pharmaceutical Press, London, 1994, 141-142.

Zhao et al., The influence of swelling capacity of superdisintegrants in different pH media on the dissolution of hydrochlorothiazide from directly compressed tablets. AAPS PharmSciTech. Sep. 20, 2005;6(1):E120-6.

Fisman et al: "C l i n i c a l pharmacology o f senile dementia" Jan. 1, 1981, Progress in Neuro-Psychopharmacology, Pergamon Press, Oxford, GB, pp. 447-457.

Hellner K A et al: "Mode of action Xanthinol-Nicotinate on the human ERG" Nov. 25, 1973, Experimental Eye Research, Academic Press Ltd., London, p. 391.

Maxwell AJ et al.: Randomized trial of a medical food for the dietary management of chronic, stable angina. J Am Coll Cardiol. Jan. 2, 2002;39(1):37-45.

Nahaya, N: "Short-term Oral Administration of L-Arginine Improved Hemodynamics and Exercise Capacity in Patients with precapillary Pulmonary Heypertension" Am J Respir Crit Care Med, vol. 163, 2001, pp. 887-891.

Supplementary European Search Report for EP 06 77 5120.

Miller Al. The Effects of a Sustained-Release L-Arginine Formulation on Blood Pressure and Vascular Compliance in 29 Healthy Individuals, Alt. Med. Review 11:23-29 (2006).

Cameron Og et al., Effects of Yohimbine on Cerebral Blood Flow, Symptoms, and Physiological Functions in Humans, Psychosomatic Medicine 62:549-59 (2000).

* cited by examiner

RAPIDLY DISSOLVING SOLID ORAL DOSAGE FORM FOR DELIVERY OF COMPOSITION FOR INCREASING NITRIC OXIDE ACTIVITY

RELATED APPLICATIONS

The application is related to U.S. Provisional Patent Application Ser. No. 60/776,325 entitled "Compositions and method for increasing bioavailability of compositions for performance improvement", filed Feb. 23, 2006, the disclosure of which is hereby fully incorporated by reference.

FIELD OF THE INVENTION

The present invention relates to a solid oral dosage form which rapidly dissolves, quickly releasing a composition directed at increasing nitric oxide activity. The invention provides a method for reducing the disintegration time of a solid oral dosage form comprising biologically active ingredients directed at increasing nitric oxide activity.

BACKGROUND OF THE INVENTION

Although much research in drug delivery is currently directed at developing controlled time-released systems, the most common form of solid oral dosage delivery systems are those intended to be swallowed and dissolved rapidly in the mouth or gastrointestinal tract. It is often desirable to achieve fast release of active compounds of solid oral dosage forms. In order to facilitate the rapid release of active compounds disintegrants are often incorporated into the formulation of a tablet or capsule. Disintegrants are substances or mixtures of substances that are added to solid oral dosage forms such as tablets and capsules which facilitate the break-up or disintegration of the tablet or capsule contents into smaller particles which may dissolve more rapidly. Although the exact mechanism of disintegration is still unclear, water penetration is an indispensable step and nearly all disintegrants swell (Zhao N, Augsburger L L. The influence of swelling capacity of super-disintegrants in different pH media on the dissolution of hydrochlorothiazide from directly compressed tablets. AAPS PharmSciTech. 2005 Sep. 20; 6(1):E120-6).

Nitric Oxide (NO) is a small reactive radical gas secreted by cells as a signaling molecule (Nathan C. Nitric oxide as a secretory product of mammalian cells. FASEB J. 1992 September; 6(12):3051-64). NO activity is largely controlled by regulating the factors responsible for synthesizing NO—Nitric Oxide Synthases (NOSs), such as the precursor molecules. All major nitric oxide synthase (NOS) isoforms and splice variants, including a muscle-specific splice variant, are expressed in the skeletal muscles of all mammals (Stamler J S, Meissner G. Physiology of nitric oxide in skeletal muscle. Physiol Rev. 2001 January; 81(1):209-237). Furthermore, the inner lining, or endothelium, of blood vessels uses NO to signal the surrounding smooth muscle to relax. This has the effect of dilating the artery increasing blood flow.

Muscle activation, i.e. contraction, has been correlated with NO signaling. NO production is increased in contracting muscle (Kobzik L, Reid M B, Bredt D S, Stamler J S. Nitric oxide in skeletal muscle. Nature. 1994 Dec. 8; 372(6506): 546-8) and conversely, reducing muscle activity lowers NO levels (Tidball J G, Lavergne E, Lau K S, Spencer M J, Stull J T, Wehling M. Mechanical loading regulates NOS expression and activity in developing and adult skeletal muscle. Am J Physiol. 1998 July; 275(1 Pt 1):C260-6). Furthermore, NO has been shown to be involved in glucose uptake in muscles undergoing exercise (Bradley S J, Kingwell B A, McConell G K. Nitric oxide synthase inhibition reduces leg glucose uptake but not blood flow during dynamic exercise in humans. Diabetes. 1999 September; 48(9):1815-21). Additionally, NO activity is increased by insulin and insulin-like growth factors which also stimulate the uptake of glucose (Kaliman P, Canicio J, Testar X, Palacin M, Zorzano A. Insulin-like growth factor-II, phosphatidylinositol 3-kinase, nuclear factor-kappaB and inducible nitric-oxide synthase define a common myogenic signaling pathway. J Biol Chem. 1999 Jun. 18; 274(25):17437-44)

Exogenous NO in humans has been shown to result in increases in measured strength (Folland J P, Maas H, Jones D A. The influence of nitric oxide on in vivo human skeletal muscle properties. Acta Physiol Scand. 2000 June; 169(2): 141-8).

Thus, in muscles, NO is a signaling molecule which increases blood flow, increases glucose uptake and increases strength. Therefore, in terms of athletic performance it would be advantageous to increase and sustain levels of NO. Furthermore, it would be advantageous to expedite the increase of NO levels and activity through rapid delivery of NO-modulating compositions.

SUMMARY OF THE INVENTION

The foregoing needs and other needs and objectives that will become apparent for the following description are achieved in the present invention which comprises the formulation of a rapidly dissolving solid oral dosage form for the delivery of a dietary supplement directed at increasing nitric oxide activity in the body of an individual, e.g. a human or an animal. The present invention provides a dietary supplement comprising Arginine or derivatives thereof and Xanthinol Nicotinate or derivatives thereof wherein active constituents of said dietary supplement may be fine-milled. The dietary supplement of the present invention further comprises Croscarmellose and/or Crospovidone, wherein said Croscarmellose or Crospovidone act as agents of disintegration in a solid oral dosage form. The present invention also provides a method of reducing the dissolution and disintegration time of a dietary supplement comprising at least Arginine or derivatives thereof.

DETAILED DESCRIPTION OF THE INVENTION

The present invention, according to various embodiments thereof, is directed to a rapidly dissolving and disintegrating solid oral dosage form for the delivery of dietary supplements comprising at least Arginine or derivatives thereof wherein active constituents of said dietary supplement may be fine-milled. According to various embodiments of the present invention, the dietary supplement may further include Croscarmellose and/or Crospovidone as disintegrant agents. A method of decreasing the dissolution and disintegration time of dietary supplements comprising Arginine or derivatives thereof is also provided. Furthermore, the present invention provides a dietary supplement which comprises Arginine or derivatives thereof and Xanthinol Nicotinate or derivatives thereof.

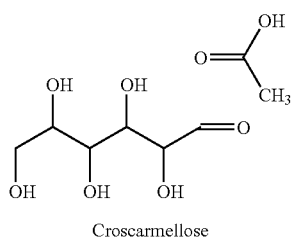

Croscarmellose

Croscarmellose (CAS No. 9000-11-7) is a polymer of cross linked carboxymethyl cellulose sodium. It is a hydrophilic, insoluble and highly absorbent material capable of excessive swelling in solution conceptually similar to a sponge. These properties make it useful in drug delivery systems as a disintegrant agent in solid dosage forms, offering improved bioavailability through enhanced dissolution of incorporated active compounds. As a tablet disintegrant, Croscarmellose is typically used at concentrations from 0.5 to 5% w/w (Wade A, Weller P J. Handbook of Pharmaceutical Excipients, Second Edition, The Pharmaceutical Press, London, 1994, 141-142).

U.S. Pat. No. 6,599,530 entitled "Oral compacted composition comprising catechol derivatives" purports to describe an oral composition for fast delivery of entacapone and nitecapone comprising at least 6% Croscarmellose.

U.S. Pat. No. 6,245,352 entitled "Pharmaceutical formulation" discloses a pharmaceutical composition comprising the anticancer drug tamoxifen. Croscarmellose is used as the disintegrant in concentrations up to 3% in various formulations are described.

U.S. Pat. No. 4,781,925 titled "Calcium supplement compressed tablets" purports to describe a calcium supplement tablet with improved disintegration characteristics comprising 0.5-1% Croscarmellose.

U.S. Pat. No. 5,955,107 entitled "Pharmaceutical suspension tablet compositions" provides the formulation of a generic tablet to deliver pharmacologically active ingredients including vitamins. The disclosed composition includes Croscarmellose at a concentration of 1-6%.

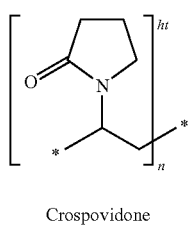

Crospovidone

Crospovidone (CAS No. 9003-39-8) is a hydrophilic synthetic homopolymer of cross-linked N-vinyl-2-pyrrolidone. It is completely insoluble in water, acids, alkalis and all organic solvents. As with most disintegrants, Crospovidone swells in aqueous solution. Crospovidone has been used to manufacture hard tablets which dissolve within 33 seconds (Shu T, Suzuki H, Hironaka K, Ito K. Studies of rapidly disintegrating tablets in the oral cavity using co-ground mixtures of mannitol with crospovidone. Chem Pharm Bull (Tokyo). 2002 February; 50(2):193-8).

U.S. Pat. No. 7,081,255 entitled "Antifungal compositions with improved bioavailability" purports to describe an oral composition to deliver the antifungal itraconazole. The solid dosage form includes 8.49% Crospovidone.

U.S. Pat. No. 6,599,531 entitled "Method of making ibuprofen and narcotic analgesic compositions" purports to describe the formulation of a solid dosage form tablet to deliver ibuprofen and hydrocodone bitartrate comprising from 4-10% of one of croscarmellose sodium, crospovidone or sodium starch glycolate as a disintegrant.

U.S. Pat. No. 7,049,283 titled "Pharmaceutical compositions for the oral delivery of pharmacologically active agents" purports to describe the use of crospovidone or povidone as the disintegrant at a concentration of 0.5-50% in formulations to deliver bone disease medication.

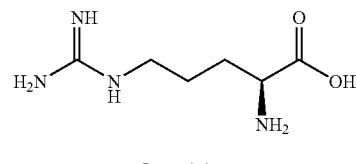

L-Arginine

L-Arginine (CAS No. 74-79-3) is considered a semi-essential amino acid. Normally L-Arginine is synthesized in sufficient amounts by the body. However, conditions and circumstances are known wherein L-Arginine supplementation is required.

L-Arginine participates in several important metabolic processes (Barbul A. Arginine: biochemistry, physiology, and therapeutic implications. JPEN J Parenter Enteral Nutr. 1986 March-April; 10(2):227-38). As such is known that L-Arginine is a precursor for the synthesis of proteins, other amino acids, urea, creatine and nitric oxide (NO) (Appleton J. Arginine: Clinical potential of a semi-essential amino. Altern Med Rev. 2002 December; 7(6):512-22).

As a precursor to NO, L-Arginine plays an important role in regulating cardiovascular endothelium-dependent processes. Many of the therapeutic effects of L-Arginine are likely due to its role as a NO precursor (Preli R B, Klein K P, Herrington D M. Vascular effects of dietary L-arginine supplementation. Atherosclerosis. 2002 May; 162(1):1-15). Moreover, L-Arginine has been shown to improve endothelial-dependent dilatation and reduce monocyte adhesion to endothelial cells, both of which benefit patients with advanced coronary artery disease (Adams M R, McCredie R, Jessup W, Robinson J, Sullivan D, Celermajer D S. Oral L-arginine improves endothelium-dependent dilatation and reduces monocyte adhesion to endothelial cells in young men with coronary artery disease. Atherosclerosis. 1997 Mar. 21; 129(2):261-9). The endothelial dysfunction associated with chronic heart failure has been corrected by oral L-Arginine supplementation (Rector T S, Bank A J, Mullen K A, Tschumperlin L K, Sih R, Pillai K, Kubo S H. Randomized, double-blind, placebo-controlled study of supplemental oral L-arginine in patients with heart failure. Circulation. 1996 Jun. 15; 93(12):2135-41) and in mice, it has been shown to increase aerobic exercise capacity and NO production (Maxwell A J, Ho H V, Le C Q, Lin P S, Bernstein D, Cooke J P. L-arginine enhances aerobic exercise capacity in association with augmented nitric oxide production. J Appl Physiol. 2001 March; 90(3):933-8). In patients with heart failure L-Arginine supplementation increases impaired exercise-induced vasodilation (Kubota T, Imaizumi T, Oyama J, Ando S, Takeshita A. L-arginine increases exercise-induced vasodilation of the forearm in patients with heart failure. Jpn Circ J. 1997 June; 61(6):471-80). L-Arginine supplementation in conjunction with exercise results in additive effects on vasodilatation, which is consistent with the mechanism of each treatment effecting different points of NO signaling (Hambrecht R, Hilbrich L, Erbs S, Gielen S, Fiehn E, Schoene N, Schuler G. Correction of endothelial dysfunction in chronic heart failure: additional effects of exercise training and oral L-arginine supplementation. J Am Coil Cardiol. 2000 Mar. 1; 35(3):706-13).

Short-term L-Arginine supplementation improves blood flow and exercise capacity in patients with Precapillary Pulmonary Hypertension, a rare disease characterized by high pulmonary artery pressure (Nagaya N, Uematsu M, Oya H, Sato N, Sakamaki F, Kyotani S, Ueno K, Nakanishi N, Yamagishi M, Miyatake K. Short-term oral administration of L-arginine improves hemodynamics and exercise capacity in patients with precapillary pulmonary hypertension. Am J Respir Crit Care Med. 2001 March; 163(4):887-91).

Furthermore, research has shown that reduced availability of L-Arginine may result in reduced NO production (Hallemeesch M M, Lamers W H, Deutz N E. Reduced arginine availability and nitric oxide production. Clin Nutr. 2002 August; 21 (4):273-9) thereby indicating that in order to achieve increased NO levels, L-Arginine supplement is required. Therefore, it is desirable to ensure adequate L-Arginine availability to facilitate NO function and production.

In an embodiment of the present invention, which is set forth in greater detail in the examples below, the dietary supplement includes Arginine or derivatives thereof. A serving of the dietary supplement may include from about 1.000 g to about 6.000 g of Arginine or derivatives thereof. The preferred dosage of a serving of the dietary supplement comprises about 3.275 g of Arginine or derivatives thereof.

Xanthinol Nicotinate

Xanthinol nicotinate is one of several forms of the vitamin Niacin (vitamin B3). It easily passes through the cell membrane and is considered the most potent form of Niacin. Pharmaceutically, Xanthinol nicotinate is classified as a vasodilator.

In patients with peripheral arterial obliterative disease, Xanthinol nicotinate was found to have anti-platelet and thrombolytic actions accompanied by an increase in the release of NO (Bieron K, Swies J, Kostka-Trabka E, Gryglewski R J. Thrombolytic and antiplatelet action of xanthinol nicotinate (Sadamin): possible mechanisms. J Physiol Pharmacol. 1998 June; 49(2):241-9). Xanthinol nicotinate may also have the effects of enhancing cellular metabolism and increasing oxygen supply which may be the mechanism of improvements in both short- and long-term memory associated with 500 mg of Xanthinol nicotinate three times per day for eight weeks in a double blind study (Loriaux S M, Deijen J B, Orlebeke J F, De Swart J H. The effects of nicotinic acid and xanthinol nicotinate on human memory in different categories of age. A double blind study. Psychopharmacology (Berl). 1985; 87(4):390-5).

In an embodiment of the present invention, which is set forth in greater detail in the examples below, the dietary supplement includes Xanthinol nicotinate or derivatives thereof. A serving of the dietary supplement may include from about 0.0500 g to about 1.5000 g of Xanthinol nicotinate or derivatives thereof. The preferred dosage of a serving of the dietary supplement comprises about 0.2325 g of Xanthinol nicotinate or derivatives thereof.

Fine-Milling of Active Constituents

As set forth above, the dosage form of the dietary supplement, in accordance with the example embodiments set forth below, may be provided in accordance with customary processing techniques for herbal and/or dietary supplements, wherein the active ingredients are suitably processed into a desired form. In accordance with various embodiments of the present invention, one or more ingredients of the diet supplement are processed so as to form fine-milled particles. For instance, in various embodiments, one or more ingredients of the dietary supplemental are processed by a large-scale dry milling technique that produces fine particles, preferably known as fine-milled particles. The use of dry milling techniques, in combination with excipients and polymers, to form fine-milled particles has been shown to improve flow and dispersability, stability, resistance to moisture, bioavailability, and dissolution/release properties. Formulations benefit by containing fine-milled particles for the purpose of providing the one or more ingredients in particle sizes that optimize one or more of the flow and dispersability, stability, resistance to moisture, bioavailability, and dissolution/release properties of the one or more ingredients in a dietary supplement. In vitro tests designed to simulate the environment of stomach were preformed to test the dissolution rate of fine-milled particle tablets versus non-fine-milled. These test showed that in tablets produced from fine-milled particles the time to 100% dissolution was approximately 15 minutes. In the case of non-fine-milled particle compositions, only 90% dissolution was observed after 120 minutes. In preferred embodiments, the dietary supplemental contains fine-milled particles having and average size between about 50 nm and about 2 nm.

U.S. Provisional Patent Application 60/776,325 discloses a method for improving the absorption, palatability, taste, texture, and bioavailability of compounds by increasing the solubility of said compounds in proprietary formulations for the purposes of enhancing or improving muscle size, growth and/or recovery time and/or weight loss. The increased bioavailability of the compound or ingredients is achieved by reducing the particle size via "fine-milling" thereby increasing the surface area-to-volume ratio each particle, thus increasing the rate of dissolution. The compositions and methods disclosed promote increased bioavailability by increasing the total surface area of poorly soluble particles, thereby increasing the rate of absorption.

As used herein the, term "fine-milled" and/or "fine-milling" refers to the process of micronization. Micronization is a mechanical process that involves the application of force to a particle, thereby resulting in a reduction in the size of the particle. The force, in the case of micronization may be applied in any manner such as, e.g., the collision of particles at high rates of speed, grinding, or by an air-jet micronizer. In preferred embodiments, fine-milled particles are obtained by jet-milling with nitrogen and compressed air.

As used herein, term "particle size" refers to the diameter of the particle. The term "average particle size" means that at least 50% of the particles in a sample will have the specified particle size. Preferably, at least 80% of the particles in a sample will have the specified particle size, and more preferably, at least 90% of the particles in a given sample will have the specified particle size.

The size of a particle can be determined any of the methods known within the art. Methods for particle size determination which may be employed are for example, e.g., sieves, sedimentation, electrozone sensing (Coulter counter), microscopy, and/or Low Angle Laser Light Scattering. The preferred methods for the particle size determination of the present invention are those methods which are most commonly used in the pharmaceutical industry, such as laser diffraction, e.g., via light scattering Coulter Delsa 440SX.

The fine-milling process may be employed in the processing of one or more of the ingredients of the present invention in the dosage forms of tablets, e.g., immediate-release film coated, modified-release and fast-dissolving; capsules or tablets, e.g., immediate-release and modified-release; liquid dispersions; powders; drink mixes, etc.

The present invention concerns a solid dosage form for rapidly releasing a dietary supplement directed at increasing nitric oxide activity in the body of an individual, e.g. a human or an animal. Typically, solid oral dosage forms include tablets, chewable tablets, capsules, and soft gelatin capsules. The preferred dosage forms of the present invention comprises tablets or caplets. Moreover, the dietary supplement of the present invention may be consumed as a stand-alone dietary supplement or may be included as a component of a larger composition.

Furthermore, the solid dosage form and composition may be provided in accordance with customary processing techniques for herbal and dietary supplements in any of the forms mentioned above. Additionally, the solid dosage form and composition set forth in the examples embodiments herein may contain any appropriate number and type of excipients, as is well-known in the art.

Preferably, the solid dosage form is consumed by an individual, e.g. a human or an animal in accordance with the following method: As a dietary supplement, a serving of said solid dosage form consisting of three tablets may be taken with an 8 oz. glass of water at least once daily. When used in conjunction with an exercise program, one serving is to be taken prior to exercise. In this manner the solid dosage form may be rapidly dissolved and effectively and efficiently release contained biologically active components. In an embodiment of the present invention the biologically active components to be released are Arginine or derivatives thereof and Xanthinol Nicotinate or derivatives thereof. In another embodiment of the present invention the biologically active component to be released is Arginine. The present invention is directed at rapidly providing components for increasing nitric oxide activity in an individual e.g. a human or an animal.

Although the following examples illustrate the practice of the present invention in three of its embodiments, the examples should not be construed as limiting the scope of the invention. Other embodiments will be apparent to one of skill in the art from consideration of the specifications and examples.

Example 1

A serving of the dietary supplement comprises: about 0.0833 g of fine-milled L-Arginine base, about 3.275 g of L-Arginine, about 0.2325 g of Xanthinol nicotinate, about 0.0800 g of Croscarmellose sodium, about 0.0100 g of L-Arginine ketoisocaproic acid and about 0.0027 g of Yohimbine HCl. The dietary supplement may additionally further comprise the following ingredients: Hydroxypropyl cellulose, Microcrystalline cellulose, Vegetable stearine, Magnesium stearate, Silica, Polyvinyl alcohol, Polyethylene glycol, FD&C Red No. 40, Talc, Titanium dioxide and FD&C Blue No. 2.

Directions: As a dietary supplement, one serving comprising three tablets is to be consumed at least once daily with 8 oz. of an aqueous medium. When used in conjunction with a regular exercise program, one daily serving to be consumed prior to exercise.

Example 2

A serving of the dietary supplement comprises: about 0.0833 g of fine-milled L-Arginine base, about 3.275 g of L-Arginine, about 0.2325 g of Xanthinol nicotinate, about 0.1400 g of Crospovidone (PVP), about 0.0100 g of L-Arginine ketoisocaproic acid and about 0.0027 g of Yohimbine HCl. The dietary supplement may additionally further comprise the following ingredients: Hydroxypropyl cellulose, Microcrystalline cellulose, Vegetable stearine, Magnesium stearate, Silica, Polyvinyl alcohol, Polyethylene glycol, FD&C Red No. 40, Talc, Titanium dioxide and FD&C Blue No. 2.

Directions: As a dietary supplement, one serving comprising three tablets is to be consumed at least once daily with 8 oz. of an aqueous medium. When used in conjunction with a regular exercise program, one daily serving to be consumed prior to exercise.

Example 3

A serving of the dietary supplement comprises: about 0.0833 g of fine-milled L-Arginine base, about 3.275 g of L-Arginine, about 0.2325 g of Xanthinol nicotinate, about 0.0200 g of Croscarmellose sodium, about 0.1000 g og Crospovidone (PVP), about 0.0100 g of L-arginine ketoisocaproic acid and about 0.0027 g of Yohimbine HCl. The dietary supplement may additionally further comprise the following ingredients: Hydroxypropyl cellulose, Microcrystalline cellulose, Vegetable stearine, Magnesium stearate, Silica, Polyvinyl alcohol, Polyethylene glycol, FD&C Red No. 40, Talc, Titanium dioxide and FD&C Blue No. 2.

Directions: As a dietary supplement, one serving comprising three tablets is to be consumed at least once daily with 8 oz. of an aqueous medium. When used in conjunction with a regular exercise program, one daily serving to be consumed prior to exercise.

In the foregoing specification, the invention has been described with specific embodiments thereof, however, it will be evident that various modifications and changes may be made thereto without departing from the broader spirit and scope of the invention.

What is claimed is:

1. A dietary supplement comprising L-Arginine, Xanthinol Nicotinate, and yohimbine.

2. The dietary supplement of claim 1, further comprising Crospovidone or derivatives thereof.

3. The dietary supplement of claim, 1 further comprising Croscarmellose or derivatives thereof.

4. The dietary supplement of claim 1, wherein from about 1% to about 10% of the L-Arginine is fine-milled.

5. The dietary supplement of claim 4, wherein the L-Arginine that is fine-milled are between 2 nm and 50 nm in average particle size.

6. A method of decreasing the disintegration time of tablet comprising at least Arginine, Xanthinol Nicotinate and yohimbine as active ingredients, the method comprising adding a disintegrant to said composition.

7. The method of claim 6 wherein hydrophilic Croscarmellose or derivatives thereof are used as a tablet disintegrant.

8. The method of claim 7 wherein said hydrophilic Croscarmellose absorbs a liquid and swells resulting in the promotion of the dissolution and disintegration of a tablet.

9. The method of claim 7 wherein said Crocarmellose is embedded in and in communication with the constituents of a tablet wherein the exploitation the hydrophilic properties of Croscarmellose results in a rapid dissolution and disintegration of said tablet.

10. The method of claim 9 wherein the time to bioavailability of said active ingredients is decreased.

11. The method of claim 6 wherein hydrophilic Crospovidone or derivatives thereof are used as a tablet disintegrant.

12. The method of claim 11 wherein said hydrophilic Crospovidone absorbs liquids and swells resulting in the promotion of the dissolution and disintegration of a tablet.

13. The method of claim 11 wherein said Crospovidone is imbedded in and in communication with the constituents of a table wherein the exploitation the hydrophilic properties of Croscarmellose results in a rapid dissolution and disintegration of said tablet.

14. The method of claim 13 wherein the time to bioavailability of said active ingredients is decreased.

15. A method comprising the step of the administering to a human or an animal comprising a dietary supplement according to claim 1.

16. A method comprising the step of the administering to a human or an animal comprising a dietary supplement according to claim 2.

17. A method comprising the step of the administering to a human or an animal comprising a dietary supplement according to claim 3.

18. A method comprising the step of the administering to a human or an animal comprising according a dietary supplement to claim 2 wherein said Croscarmellose decreases the dissolution and disintegration time when said dietary supplement is administered in the form of a tablet.

19. A method comprising the step of the administering to a human or an animal comprising according a dietary supplement to claim 3 wherein said Crospovidone decreases the dissolution and disintegration time when said dietary supplement is administered in the form of a tablet.

20. The dietary supplement according to any of claim 1-3 or 5, wherein said dietary supplement is in a solid oral dosage form selected from the group consisting of tablets, capsules or caplets.

21. The dietary supplement according to claim 20, wherein at least a portion of the L-Arginine is present within an immediate-release film coating.

22. The dietary supplement of claim 1, further comprising Crospovidone or derivatives thereof, and Croscarmellose or derivatives thereof.

23. A dietary supplement comprising from about 1.0 g to about 6.0 g of L-Arginine, from about 0.050 g to about 1.50 g of Xanthinol Nicotinate, and about 0.0027 g of yohimbine HCl.

24. The dietary supplement of claim 23, further comprising Crospovidone or derivatives thereof.

25. The dietary supplement of claim 23, further comprising Croscarmellose or derivatives thereof.

26. The dietary supplement of claim 23, further comprising Crospovidone or derivatives thereof, and Croscarmellose or derivatives thereof.

27. The composition of claim 23, wherein from about 1% to about 10% of the L-Arginine is fine-milled.

28. The dietary supplement of claim 27, wherein the L-Arginine that is fine-milled is between 2 nm and 50 nm in average particle size.

29. The dietary supplement according to any of claims 23 through 25, wherein said dietary supplement is in a solid oral dosage form selected from the group consisting of tablets, capsules or caplets.

30. The dietary supplement according to claim 1, wherein the dietary supplement comprises a solid oral dosage form.

31. The dietary supplement according to claim 27, wherein the dietary supplement comprises a solid oral dosage form.

32. The dietary supplement according to claim 31, wherein the solid oral dosage form is selected from the group consisting of tablets, capsules or caplets.

33. The dietary supplement according to claim 32, wherein the tablets have a 100% dissolution time of about 15 minutes.

34. The dietary supplement according to claim 32, wherein at least a portion of the L-Arginine is present within an immediate-release film coating.

35. The dietary supplement according to claim 23, wherein the dietary supplement comprises a solid oral dosage form.

36. The dietary supplement according to claim 4, wherein the dietary supplement comprises a solid oral dosage form.

37. The dietary supplement according to claim 36, wherein the solid oral dosage form is selected from the group consisting of tablets, capsules or caplets.

38. The dietary supplement according to claim 37, wherein the tablets have a 100% dissolution time of about 15 minutes.

39. The dietary supplement according to claim 37, wherein at least a portion of the L-Arginine is present within an immediate-release film coating.

* * * * *